United States Patent [19]

Ogasawara

[11] Patent Number: 4,489,741
[45] Date of Patent: Dec. 25, 1984

[54] WASHING APPARATUS FOR AN ENDOSCOPE

[75] Inventor: Tadahiko Ogasawara, Tokyo, Japan

[73] Assignee: Olympus Optical Co., Ltd., Tokyo, Japan

[21] Appl. No.: 471,316

[22] Filed: Mar. 2, 1983

[30] Foreign Application Priority Data

Mar. 11, 1982 [JP] Japan .................................. 57-38288

[51] Int. Cl.³ ................................................. B08B 3/04
[52] U.S. Cl. ..................................... 134/179; 239/225
[58] Field of Search ............... 134/104, 166 C, 167 C, 134/170, 171, 172, 179; 239/225

[56] References Cited

U.S. PATENT DOCUMENTS

| | | | |
|---|---|---|---|
| 287.508 | 10/1883 | Didiot | 239/225 |
| 534,863 | 2/1895 | Remer et al. | 239/225 |
| 3,770,203 | 11/1973 | Dyar | 134/179 |
| 4,278,101 | 7/1981 | Tanaka et al. | 134/167 C |
| 4,281,646 | 8/1981 | Kinoshita | 134/104 |

FOREIGN PATENT DOCUMENTS 48-13187 4/1973 Japan .
52-87066 6/1977 Japan .

Primary Examiner—John W. Shepperd
Assistant Examiner—Renee S. Kidorf

[57] ABSTRACT

An apparatus for washing an endoscope by spraying washing liquid thereagainst is disclosed, which comprises a housing including a washing tank, and a rotary body rotatably mounted on a central portion of the washing tank. The rotary body has a horizontal cylindrical inner space formed in its upper portion. The rotary body carries an upper nozzle, which includes a cylindrical body capable of being retracted into the cylindrical space and a nozzle tip provided on the free end of the cylindrical member and directed downwards. The cylindrical member has a piston provided on its rear end and biased by a spring in the direction of retraction of the cylindrical member into the cylindrical space. The rotary body also carries a lower nozzle secured to its lower portion and directed upwards. When pressurized washing liquid is supplied to the upper and lower nozzles, it is sprayed from these nozzles against an endoscope which is set at a level between these nozzles. A this time, the cylindrical member is extended out of the rotary body against the biasing force of the spring by the pressure of the washing liquid.

6 Claims, 4 Drawing Figures

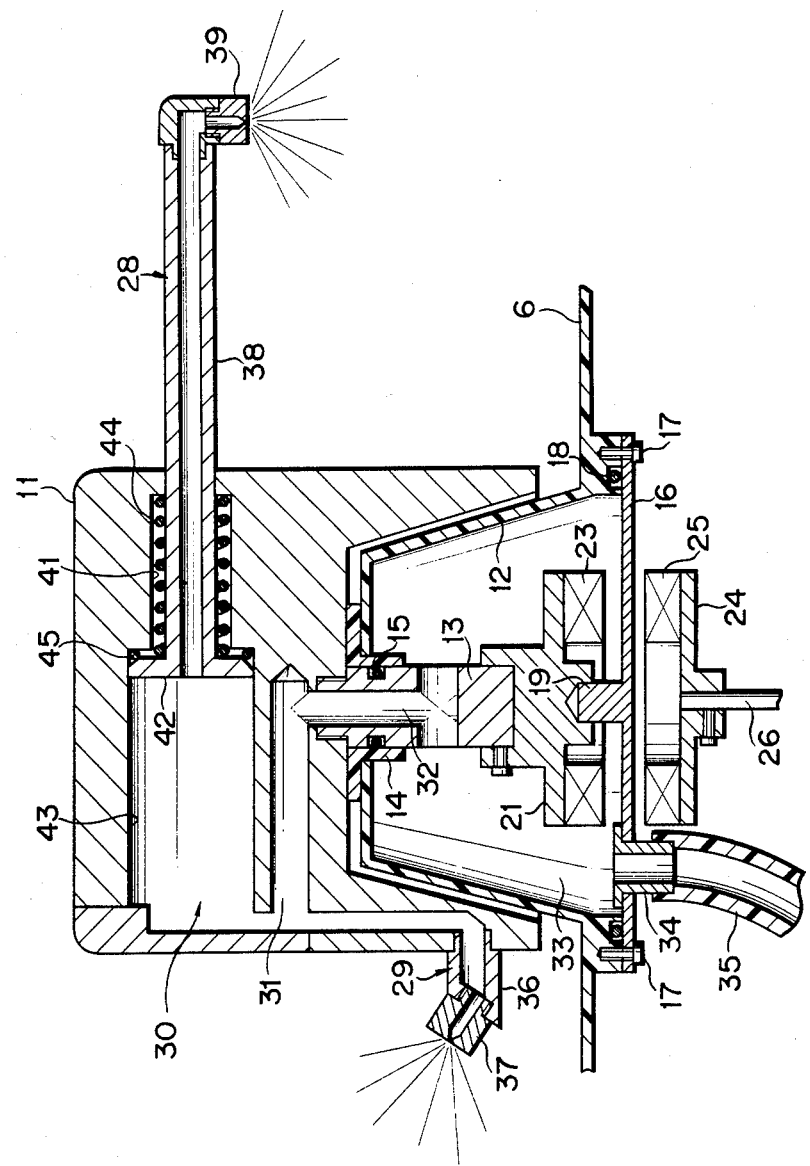

WASHING APPARATUS FOR AN ENDOSCOPE

BACKGROUND OF THE INVENTION

This invention relates to an apparatus for washing an endoscope.

The endoscope is usually washed in a washing tank in which it is set with its elongate inserting section in a spirally wound state, and washing liquid is sprayed under pressure from a rotating nozzle assembly to wash it. In order to be able to wash the endoscope efficiently, the nozzle assembly usually includes two nozzles, i.e., an upper nozzle which is located above the endoscope in the washing tank and a lower nozzle located below the endoscope. The upper nozzle has a small projecting length so that it will not be obstructive when setting the endoscope in a washing tank. A large projecting length, on the other hand, is provided for the lower nozzle, so that the washing liquid sprayed from both the nozzles can be evenly supplied over the entire endoscope. The provision of a large projecting length of the lower nozzle, however, requires a broad bottom space of the washing tank, in which the lower nozzle can be rotated during washing. In other words, the volume of the tank must be increased that much. This means that the quantity of a disinfectant solution which is supplied into the tank for sterilizing the endoscope must be increased that much. In addition, more time is required for supplying and recovering the solution.

If the projecting length of the lower nozzle is also reduced in order to alleviate the above inconveniences, the effect of washing the entire endoscope is greatly reduced. In particular, where a lightguide cable is set together with the inserting section of the endoscope in the same washing tank for washing, in which case the area in which the washing liquid supplied for washing is increased, effective washing of the entire endoscope cannot be obtained if both the upper and lower nozzles are reduced in projecting length.

SUMMARY OF THE INVENTION

An object of the invention is to provide a washing apparatus for an endoscope wherein the endoscope can be set in the washing tank without being obstructed by the upper nozzle.

Another object of the invention is to provide a washing apparatus for an endoscope, in which the washing liquid can be distributed evenly over the entire endoscope set in the washing tank so that the endoscope can be effectively washed, and also in which the lower space of the washing tank where the disinfectant solution is retained can be reduced.

According to the present invention, there is provided a washing apparatus for an endoscope, which comprises a housing including a washing tank, a rotary body rotatably mounted in the washing tank, the rotary body having an inner space, means for supplying the washing liquid into said inner space, drive means for rotating said rotary body, an upper nozzle including a cylindrical member provided to the rotary body and communicating with the inner space, the cylindrical member being capable of being extended and retracted in a substantially horizontal direction with respect to the rotary body, and a nozzle tip provided on the free end of the cylindrical member and capable of spraying the washing liquid downwards, the cylindrical member being in an extended position when the washing liquid is spraying from the nozzle tip, a lower nozzle provided to the rotary body and communicating with the inner space, the lower nozzle being capable of spraying the washing liquid upwards from a lower part of the space of said washing tank, the endoscope being set between the upper and lower nozzles.

BRIEF DESCRIPTION OF THE DRAWINGS

FIG. 4 is an enlarged sectional view showing a rotary body and upper and lower nozzles in the same tank.

DETAILED DESCRIPTION OF THE PREFERRED EMBODIMENT

Figure 1:
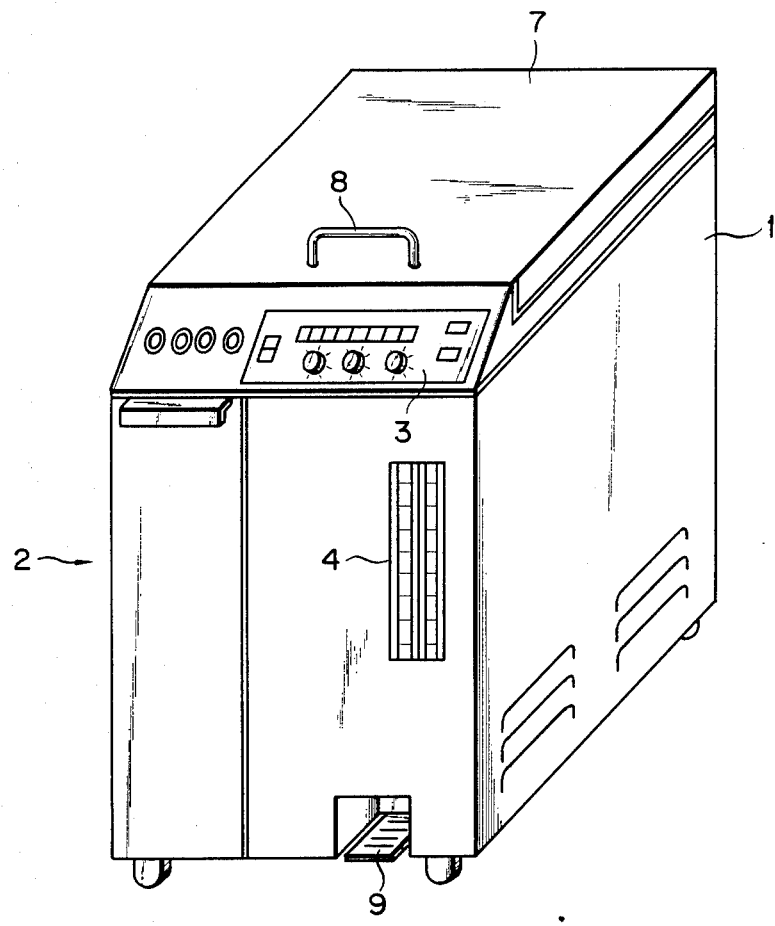
FIG. 1 is a perspective view showing a washing apparatus for an endoscope according to an embodiment of the invention.

FIG. 1 shows an embodiment of the washing apparatus for an endoscope according to the invention. The illustrated washing apparatus 2 comprises a housing 1 which has an operation panel 3 provided on its front top. An indicator 4 which indicates the quantities of a detergent and a disinfectant solution, is provided on the front of the housing 1. A washing tank 6 is provided in the housing 1, which accommodates an endoscope 5 as described later. The open top of the tank 6 is covered by a cover 7 which can be opened and closed. The cover 7 may be opened by hand by gripping a handle 8, or it may be operated by depressing a foot pedal 9.

Figure 2:
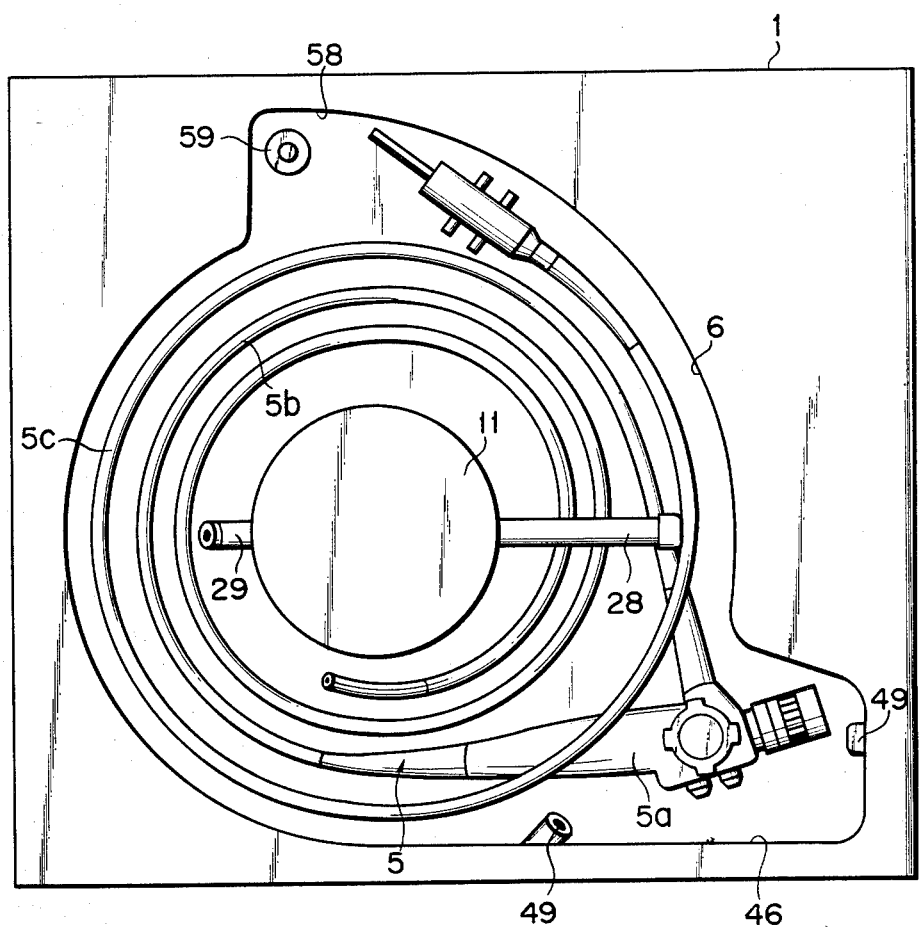
FIG. 2 is a plan view showing an endoscope set in a washing tank.
Figure 3:
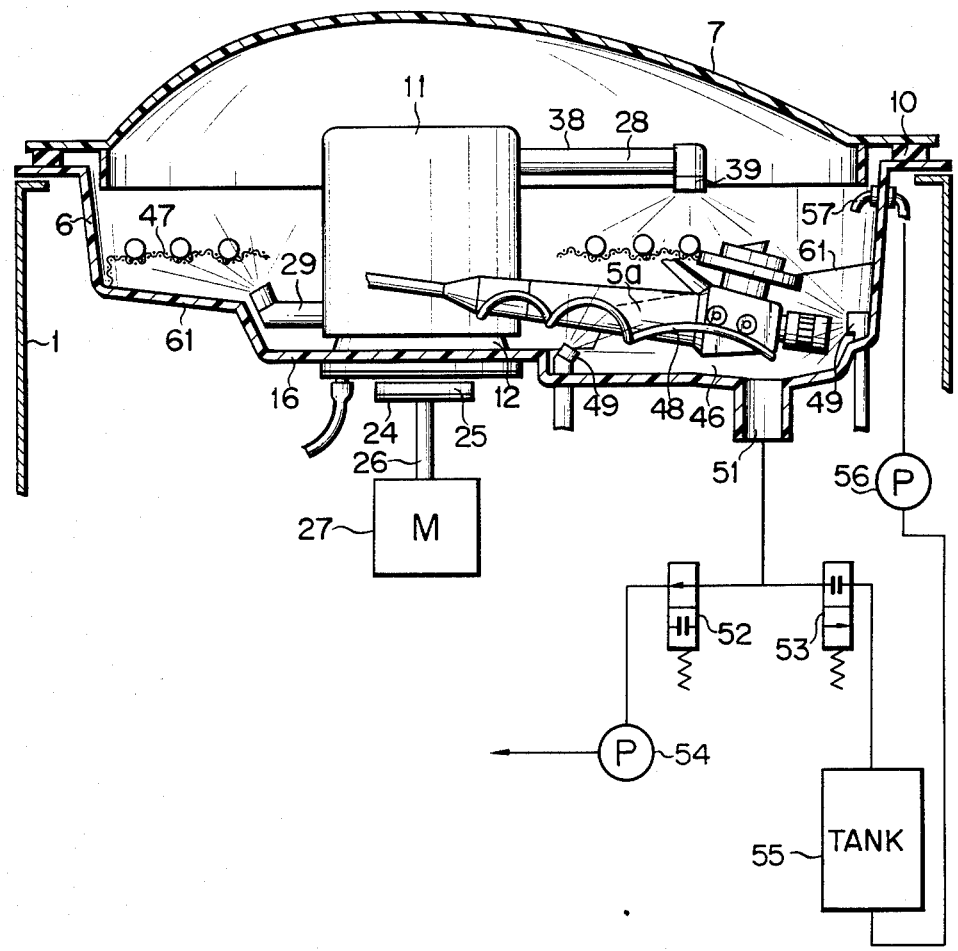
FIG. 3 is a sectional view showing the washing tank with internal parts therein.

The internal construction of the washing apparatus 2 is shown in FIGS. 2 to 4. The washing tank 6 has a substantially dish-like shape. A rotary body 11, in which an inner space 30 is defined and which has a vertical shaft 13, is mounted on a substantially central portion of the washing tank 6. As shown in FIG. 4, the bottom of the washing tank 6 has a substantially central frustoconical base portion 12 protruded upwards from the other portion. The top wall of this base portion 12 has a central circular mounting hole, in which a bearing bush 14 with a top flange is fitted. The bottom of the rotary body 11 is frustoconically recessed so that it is substantially complementary in shape to the base portion 12. The vertical shaft 13 projected from the center of the recess is secured to the rotary body 11. The shaft 13 is rotatably fitted in the bearing bush 14 so that the rotary body 11 is rotatably supported on the base portion 12. A ring-like packing 15 is provided between the shaft 13 and bush 14. The lower opening of the base portion 12 is closed by a disk-like partition member 16 made of a non-magnetic material, which is secured by screws 17 to the washing tank 6. A ring-like packing 18 is provided between the edge of the partition member 16 and the lower end, i.e., the edge, of the base portion 12. The space 33 defined by the base portion 12 and partition member 16 is thus sealed liquid-tight by the packings 15 and 18. The partition member 16 has a mounting hole formed in a suitable portion near its edge, and a tubular connector 34 with a top flange fitted in the mounting hole and secured to the partition member 16 at one end of the connector 34. A tube 35 leading from a washing liquid tank (not shown) is fitted at the other end of the connector 34. A water pump (not shown) is provided on the tube 35 to force out washing liquid from the washing liquid tank into the space 33 in the base portion 12.

A driven yoke 21 is bolted to the lower end of the rotary shaft 13, and it carries a driven magnet 23 secured to an edge portion of its underside. A thrust pin 19 projects from the top of the partition member 16. It is coaxial with the center of the rotary shaft 13, and its upper portion is fitted in a recess, which is formed in the underside of the yoke 21 and is also coaxial with the rotary shaft 13. It can withstand the thrust that is exerted when the rotary body 11 is rotated about the shaft 13. A drive yoke 24 is disposed to face the driven yoke 21 via the partition member 16. The drive yoke 24 carries a drive magnet 25 which faces the driven magnet 23. The drive yoke 24 has a shaft 26 coupled to a drive motor 27, which is operated when washing the endoscope. The drive magnet 25 supported by the drive yoke 24, and the driven magnet 23 supported by the driven yoke 21 are magnetically coupled so that the torque of the drive motor 27 can be transmitted to the rotary body 11.

The rotary shaft 13 has an axial bore coaxially extending in its upper portion and also has radial bores communicating with the lower end of the axial bore and open on its periphery. These bores form a washing liquid passage 32. The rotary body 11 has an inner space 30 which communicates with the passage 32 in the rotary shaft 13. The inner space 30 includes a cylindrical space 43 and a washing liquid passage 31. The cylindrical space 43 extends horizontally in an upper portion of the rotary body 11. It is communicated with the passage 32 in the rotary shaft 13 through the passage 31, and hence, it is communicated with the space 33 in the base portion 12. A guide hole 41 is formed in the rotary body 11 on one side thereof such that it is coaxial with and terminates in the cylindrical space 43 and has a smaller diameter than the cylindrical space 43.

The rotary body 11 has an upper nozzle 28 mounted in its upper portion and also a lower nozzle 29 mounted in its lower portion. The upper nozzle 28 includes an elongate cylindrical member 38 and a nozzle tip 39 secured to the free end of the cylindrical member 38. The cylindrical member 38 has a flange-like piston 42 integrally formed on its rear end and having substantially the same outer diameter as the diameter of the cylindrical space 43. The piston 42 is slidably fitted in the cylindrical space 43 and the cylindrical member 38 is movable through the guide hole 41. As the piston 42 is moved along the cylindrical space 43, the cylindrical member 38 is advanced and retracted along the cylindrical space 43 and guide hole 41 for the stroke corresponding to the length of the cylindrical space 43. The nozzle tip 39 mounted on the free end of the cylindrical member 38 is directed downwards. A compression coil spring 44 is provided on a rear portion of the cylindrical member 38 extending in the guide hole 41. It acts on the piston 42 and thus biases the upper nozzle 28 in the retracting direction so that the rear portion of the cylindrical member 38 retracts into the cylindrical space 43. In the absence of washing liquid in the cylindrical space 43, the upper nozzle 28 is thus held in its retracted position in the rotary body 11 by the spring 44. The force of the spring 44 is set such that the upper nozzle 28 can be moved against it in the forward direction from the rotary body 11 by the pressure of the washing liquid supplied from the water pump into the cylindrical space 43. A ring-like packing 45 is provided on a shoulder or stepped wall formed between the guide hole 41 and cylindrical space 43. It ensures a liquid-tight seal between the piston 42 and the stepped wall of the rotary body 11 while the washing liquid is supplied.

The lower nozzle 29 is mounted in the lower portion of the rotary body 11 on the side thereof opposite the guide hole 41. It includes a cylindrical member 36 having a small length mounted in the lower portion of the rotary body 11 and a nozzle tip 37 mounted on the free end of the cylindrical member 36 and directed in an upwardly inclined direction. The nozzle tip 37 and cylindrical member 36 communicate with the rotary shaft 13 through the passage 31 formed in the rotary body 11.

The endoscope 5, which is to be washed with the present embodiment of this apparatus, includes an operating section 5a, an inserting section 5b and a lightguide cable section 5c as shown in FIG. 2. It has an entirely liquid-tight construction, and it is set in the washing tank 6 on supporting means to be described later in detail. The elongate inserting and lightguide cable sections 5b and 5c are set such that they are spirally wound in opposite directions, while the operating section 5a is set in a somewhat laterally protruding increased depth portion 46 of the washing tank 6 corresponding to one corner of the housing 1. The support means noted above includes a net member 47 disposed at a level between the upper and lower nozzles 28 and 29 for supporting the inserting and lightguide cable sections 5b and 5c and a support member 48 for supporting the operating section 5a as shown in FIG. 3.

The portion 46 of the washing tank 6 is provided with a plurality of stationary washing nozzles 49 directed toward the operating section 5a that is set on the support member 48. These stationary nozzles 49 serve to jet washing liquid toward the operating section 5a, which would otherwise not receive sufficient washing liquid from the rotating upper and lower nozzles 28 and 29. They are connected to the washing liquid tank through the water pump mentioned before.

As shown in FIG. 3, the bottom of the washing tank 6 is provided with a drain port 51. A duct communicating with the drain port 51 has two branches, which are provided with respective first and second electromagnetic on-off valves 52 and 53. The first electromagnetic on-off valve 52 is normally open, while the second electromagnetic on-off valve 53 is normally closed. The first electromagnetic on-off valve 52 is coupled to a draining pump 54. The second electromagnetic on-off valve 53 is coupled to a disinfectant solution tank 55. The disinfectant tank 55 is connected through a duct provided with a water pump 56 to a nozzle 57, which is mounted in an upper portion of the peripheral wall of the washing tank 6.

As shown in FIG. 2, the washing tank 6 has another laterally protruding increased depth portion 58 formed at a position separate from the portion 46. A float switch 59 for detecting the liquid level in the washing tank 6 is provided in the protruding portion 58.

As shown in FIG. 3, the washing tank 6 further has a reduced-depth bottom portion 61 which covers an area of the bottom other than that over which the lower nozzle 29 is rotated, and which is raised upward from the other bottom portion. The reduced-depth bottom portion 61 is formed to cover the entire circumference of the bottom of the tank 6 about the rotary body 11 except for the portions 46 and 58. The reduced-depth bottom portion 61 is provided to reduce or eliminate unnecessary space in the tank 6, so that the volume of the tank 6 is greatly reduced. This means that the quantity of the disinfectant solution to be supplied into the tank 6 in a sterilizing step can be greatly reduced.

The open top of the washing tank 6 is covered by the cover 7 with a packing 10 provided between the edge of the cover 7 and the top of the washing tank 6. The packing 10 serves to prevent the leakage of the washing liquid sprayed from the nozzle tips 57 and 39 to the outside of the washing chamber which is defined by the washing tank 6 and cover 7.

Now, the operation of the washing apparatus will be described.

First, the cover 7 is opened, and the endoscope 5 to be washed and sterilized is set in the washing tank 6. At this time, the rotary body 11 having the upper and lower nozzles 28 and 29 is stationary. Also, no washing liquid is being supplied, and without washing liquid in the cylindrical space 43 the upper nozzle 28 is held in its retracted position in the cylindrical space 43 by the biasing force of the spring 44. That is, the upper nozzle 28 does not project from the rotary body 11 to such an extent that it obstructs setting the endoscope 5 on the net member 47 and support member 48. Thus, the endoscope 5 can be quickly set in the washing tank 6 without being obstructed by the upper nozzle 28.

As shown in FIG. 2, the operating section 5a of the endoscope 5 is set on the support member 48 in the tank 6 while the inserting and lightguide cable sections 5b and 5c are set on the net member 47 as mentioned earlier. After the endoscope 5 has been in the washing tank 6 in this way, the cover 7 is closed as shown in FIG. 3. Then, the operation panel 3 is operated to start the washing operation. At this time, the water pump for supplying the washing liquid is started to pump the washing liquid from the washing liquid tank into the space 33 in the base portion 12. The washing liquid entering the space 33 is led through the passages 32 and 31 so that it jets from the upper and lower nozzles 28 and 29. The endoscope 5 is thus washed by the jets of washing liquid. The washing liquid from the washing liquid tank is also supplied to the nozzles 49 to be sprayed from these nozzles against the operating section 5a. The upper and lower nozzles 28 and 29 are rotated with the rotary body 11 driven by the drive motor 27 while the washing liquid jets from them. Meanwhile, as the pressurized washing liquid is supplied into the cylindrical space 43, it forces out the piston 42 of the cylindrical member 38 of the upper nozzle 28, thus causing advancement of the upper nozzle 28 against the restoring force of the spring 44. The upper nozzle 28 is extended until it strikes and squeezes the packing 45. Since the packing 45 is squeezed, the piston 42 and rotary body 11 are held liquid-tight with respect to each other. In the extended position, the upper nozzle 28 projects from the rotary body 11 to a greater extent than does the lower nozzle 29, which is secured to the rotary body 11. The nozzle tips 39 and 37 of the respective upper and lower nozzles 28 and 29 are thus rotated along circles having different radii as shown in FIG. 2. This means that the washing liquid can be distributed more evenly in the radial direction than in the case where both the upper and lower nozzles have the same projecting length. The upper nozzle 28 jets the washing liquid downwards, while the lower nozzles 29 jets it upwards. The nozzles 49 jet the washing liquid mainly against the operating section 5a located in the portion 46 of the washing tank 6.

While the outer surfaces of the endoscope 5 are washed by the washing liquid in the above way, inner passages of the endoscope 5 such as the channel for a forceps are also washed by supplying the washing liquid through tubes (not shown) connected to them.

The washing liquid falling to the bottom of the washing tank 6 goes into to a drain port 51, and is then drained out by the draining pump 54 through the first electromagnetic on-off valve 52.

If a sterilizing step is specified, the sterilizing process is begun after the washing step is ended. The water pump 56 is operated with the first and second electromagnetic on-off valves 52 and 53 closed. The disinfectant solution in the tank 55 is thus poured from the nozzle 57 into the tank 6. It is supplied until its level is detected by the float switch 59. At this time, the endoscope 5 is entirely immersed in the disinfectant solution. The endoscope 5 is sterilized when it is left in this state for a predetermined period of time. After the sterilization is completed, the second electromagnetic on-off valve 53 is opened to return the disinfectant solution in the tank 6 into the tank 55. Afterwards, the endoscope 5 is rinsed by jets of water from the upper and lower nozzles 28 and 29 and the nozzles 49 in the same manner as in the washing step.

When the rinsing is ended, the rotaty body 11 and upper and lower nozzles 28 and 29 are stopped. Also, the upper nozzle 28 is retracted into the rotary body 11 by the biasing force of the return spring 44. The washed endoscope 5 can thus be readily taken out from the washing tank 6 without being obstructed by the upper nozzle 28.

As has been described in the foregoing, with the endoscope washing apparatus according to this invention, the upper nozzle extends out of the rotary body only while washing the endoscope, and is held retracted in the rotary body when setting in and taking out the endoscope, so that the endoscope can be readily set in and taken out. In addition, since the upper nozzle is extended during washing such that its projecting length is greater than that of the lower nozzle, the washing liquid can be sprayed against the endoscope set in the washing tank more evenly than in the prior art case where both the upper and lower nozzles have the same reduced projecting length. Thus, it is possible to clean all portions of the endoscope.

What is claimed is:

1. A washing apparatus for an endoscope which sprays washing liquid thereagainst, comprising:
a housing including a washing tank;
a rotary body rotatably mounted in said washing tank, said rotary body having an inner space;
means for supplying the washing liquid into said inner space;
drive means for rotating said rotary body;
an upper nozzle including a cylindrical member provided on said rotary body and communicating with said inner space, said cylindrical member being mounted so that it can be extended at least in part by the centrifugal force caused by the rotation of said rotary body and retracted in a substantially horizontal direction with respct to said rotary body, a sealing member for sealing said cylindrical member and said rotary body, and a nozzle tip provided on a free end of said cylindrical member and capable of spraying the washing liquid downwards, said cylindrical member being in an extended position when the washing liquid is spraying from said nozzle tip; and a lower nozzle provided on said rotary body and communicating with said inner space, said lower nozzle being capable of spraying the washing liquid upwards from a fixed position which is a lower part of the space of said washing tank, the fixed position being closer to said rotary body than said nozzle tip when the latter is located at the extended position of said cylindrical member, the endoscope being set between said upper and lower nozzles.

2. A washing apparatus for an endoscope according to claim 1, wherein said washing tank has a reduced depth bottom portion covering an area other than that over which said lower nozzle is rotated.

3. A washing apparatus for an endoscope according to claim 1, wherein said rotary body has a first shaft downwardly projecting from its bottom, and said drive means includes a second shaft disposed outside said housing and coaxial with said first shaft, magnetic coupling means respectively mounted on said first and second shafts and capable of magnetically coupling said first and second rotary shafts, and a drive source capable of rotating said second shaft.

4. A washing apparatus for an endoscope according to claim 1, which further comprises biasing means for biasing said cylindrical member in the direction of retraction of said upper nozzle into said rotary body, the biasing force of said biasing means being such that said cylindrical member can be extended by the pressure of the washing liquid supplied into said inner space.

5. A washing apparatus for an endoscope according to claim 4, wherein said inner space includes a horizontal cylindrical space formed in said rotary body, said rotary body having a guide hole coaxial with and communicating with said cylindrical space and being smaller in diameter than said cylindrical space and open at the periphery of said rotary body, said cylindrical member having a rear portion extending through said guide hole into said cylindrical space, said cylindrical member having a piston provided at its rear end and having the same outer diameter as the diameter of said cylindrical space, and said piston being movable through said cylindrical space so that said cylinrical member is extended and retracted.

6. A washing apparatus for an endoscope according to claim 5, wherein said biasing means includes a coil spring fitted on said cylindrical member and acting on said piston to bias said cylindrical member in the direction to retract said cylindrical member into said cylindrical space.

* * * * *